(12) United States Patent
Tutu

(10) Patent No.: US 10,918,088 B2
(45) Date of Patent: Feb. 16, 2021

(54) DOG DIAPER

(71) Applicant: Ama Konadu Tutu, Bronx, NY (US)

(72) Inventor: Ama Konadu Tutu, Bronx, NY (US)

(*) Notice: Subject to any disclaimer, the term of this patent is extended or adjusted under 35 U.S.C. 154(b) by 200 days.

(21) Appl. No.: 16/173,333

(22) Filed: Oct. 29, 2018

(65) Prior Publication Data

US 2019/0124889 A1   May 2, 2019

Related U.S. Application Data

(60) Provisional application No. 62/578,937, filed on Oct. 30, 2017.

(51) Int. Cl.
*A01K 23/00* (2006.01)
*A61F 13/49* (2006.01)
*A61F 13/15* (2006.01)

(52) U.S. Cl.
CPC .............. *A01K 23/00* (2013.01); *A61F 13/49* (2013.01); *A61F 2013/15186* (2013.01)

(58) Field of Classification Search
CPC ...... A01K 21/00; A01K 23/00; A01K 27/002; A61F 5/451; A61F 2013/15186; A61F 13/49
USPC .................................................. 119/867, 868
See application file for complete search history.

(56) References Cited

U.S. PATENT DOCUMENTS

| 4,353,330 A * | 10/1982 | Baumgartner | A01K 23/00 119/868 |
| 4,444,152 A * | 4/1984 | Berardo | A01K 23/00 119/868 |
| 4,709,661 A * | 12/1987 | Mayle, Jr. | A01K 23/00 119/868 |
| 4,813,949 A | 3/1989 | O'Rourke | |
| 4,969,419 A * | 11/1990 | Fong | A01K 23/00 119/868 |
| 4,996,949 A | 3/1991 | Wunderman et al. | |
| 5,146,874 A * | 9/1992 | Vidal | A01K 23/00 119/868 |
| 5,315,960 A * | 5/1994 | Lamp | A01K 23/00 119/868 |
| 5,355,836 A * | 10/1994 | Vallery | A01K 23/00 119/868 |
| 5,555,847 A | 9/1996 | Kelly | |
| 5,937,795 A * | 8/1999 | Raphael | A01K 23/00 119/868 |
| 6,368,313 B1 | 4/2002 | Howard | |
| 6,895,901 B1 | 5/2005 | Howard | |
| 6,941,897 B1 * | 9/2005 | Rosales | A01K 23/00 119/868 |
| 7,607,407 B1 * | 10/2009 | Blanch | A01K 21/00 119/868 |
| 8,192,414 B2 | 6/2012 | Solomon et al. | |

(Continued)

*Primary Examiner* — Christopher D Hutchens
*Assistant Examiner* — Brady W Frazier
(74) *Attorney, Agent, or Firm* — Olav M. Underdal; IDP Patent Services

(57) ABSTRACT

A diaper for mounting on a dog includes: a waistband, optionally with hook and loop connector portions; connector straps, including first and second top straps and first and second bottom straps; a collection bag, including a drawstring and a perforation; such that the waistband is positioned around the waist of the dog, such that the aperture of the collection bag is positioned around a rectal exit of the dog, whereby fecal matter is deposited in the interior of the collection bag when the dog defecates.

6 Claims, 8 Drawing Sheets

(56) References Cited

U.S. PATENT DOCUMENTS

| | | | |
|---|---|---|---|
| 8,342,138 B2 | 1/2013 | Hazan | |
| 8,757,101 B1* | 6/2014 | Phipps | A01K 23/00 119/868 |
| 8,992,495 B1 | 3/2015 | Howell | |
| 2003/0066495 A1 | 4/2003 | Soares et al. | |
| 2004/0074450 A1 | 4/2004 | Soares et al. | |
| 2004/0144334 A1* | 7/2004 | Berardo | A01K 23/00 119/868 |
| 2006/0124076 A1* | 6/2006 | Tseng | A01K 23/00 119/868 |
| 2007/0129702 A1 | 6/2007 | Gribben | |
| 2007/0227466 A1* | 10/2007 | Tsai | A01K 23/00 119/868 |
| 2010/0319633 A1 | 12/2010 | Moncheski | |
| 2011/0126779 A1* | 6/2011 | Walls | A01K 23/00 119/868 |
| 2011/0303162 A1* | 12/2011 | Morman | A01K 23/00 119/858 |
| 2015/0156991 A1* | 6/2015 | Dixon | A01K 23/00 119/868 |
| 2015/0189859 A1* | 7/2015 | John | A01K 23/00 119/868 |
| 2017/0112101 A1 | 4/2017 | Clark | |
| 2018/0020642 A1* | 1/2018 | Nicolas | A01K 23/00 119/868 |

\* cited by examiner

DOG DIAPER

CROSS-REFERENCE TO RELATED APPLICATIONS

This U.S. Non-Provisional application claims the benefit of U.S. Provisional Application No. 62/578,937, filed Oct. 30, 2017; all of which is hereby incorporated herein by reference in its entirety.

FIELD OF THE INVENTION

The present invention relates generally to the field of diapers, and more particularly to methods and devices for diapers for dogs and other pets.

BACKGROUND OF THE INVENTION

Diapers for dogs are available in the market but are generally designed as conventional diapers with a liquid absorbing layer and do not effectively capture fecal matter but are effective at capturing urine.

As such, considering the foregoing, it may be appreciated that there continues to be a need for novel and improved devices and methods for diapers for dogs.

SUMMARY OF THE INVENTION

The foregoing needs are met, to a great extent, by the present invention, wherein in aspects of this invention, enhancements are provided to the existing model of dog diapers.

In an aspect, a dog diaper can include:
a) a waistband;
b) a plurality of connector straps; and
c) a collection bag with an aperture providing access to an interior, such that the connector straps can be connected between the waistband and the collection bag, such that upper ends of the connector straps are connected to the waistband and lower ends of the connector straps are connected to the collection bag;
wherein the waistband, can be positioned around the waist of a dog;
such that the aperture of the collection bag is positioned around an anus/rectal exit of the dog;
whereby fecal matter will be deposited in an interior of the collection bag, when the dog sits to defecate.

In a related aspect, the waistband can be open with connector portions on first and second ends of the waistband, such that the connector portions detachably connect the first and second ends.

In a further related aspect, the connector portions can be hook and loop fasteners.

In another related aspect, the connector straps can include:
a) first and second top straps, such that a top opening between the first and second top straps provides space for a tail of the dog; and
b) first and second bottom straps, such that a bottom opening between the first and second bottom straps provides space for an external urethral opening of the dog, such that urine emitted from the external urethral opening is not collected in the collection bag.

In yet a related aspect, an upper part of the collection bag can further include a drawstring, which is mounted around a circumference of the collection bag, such that pulling on the drawstring closes the collection bag.

In yet another a related aspect, an upper part of the collection bag can further include a perforation around a second circumference of the collection bag, such that pulling on the collection bag can release a lower part of the collection bag by tearing the lower part of at the perforation.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. In addition, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
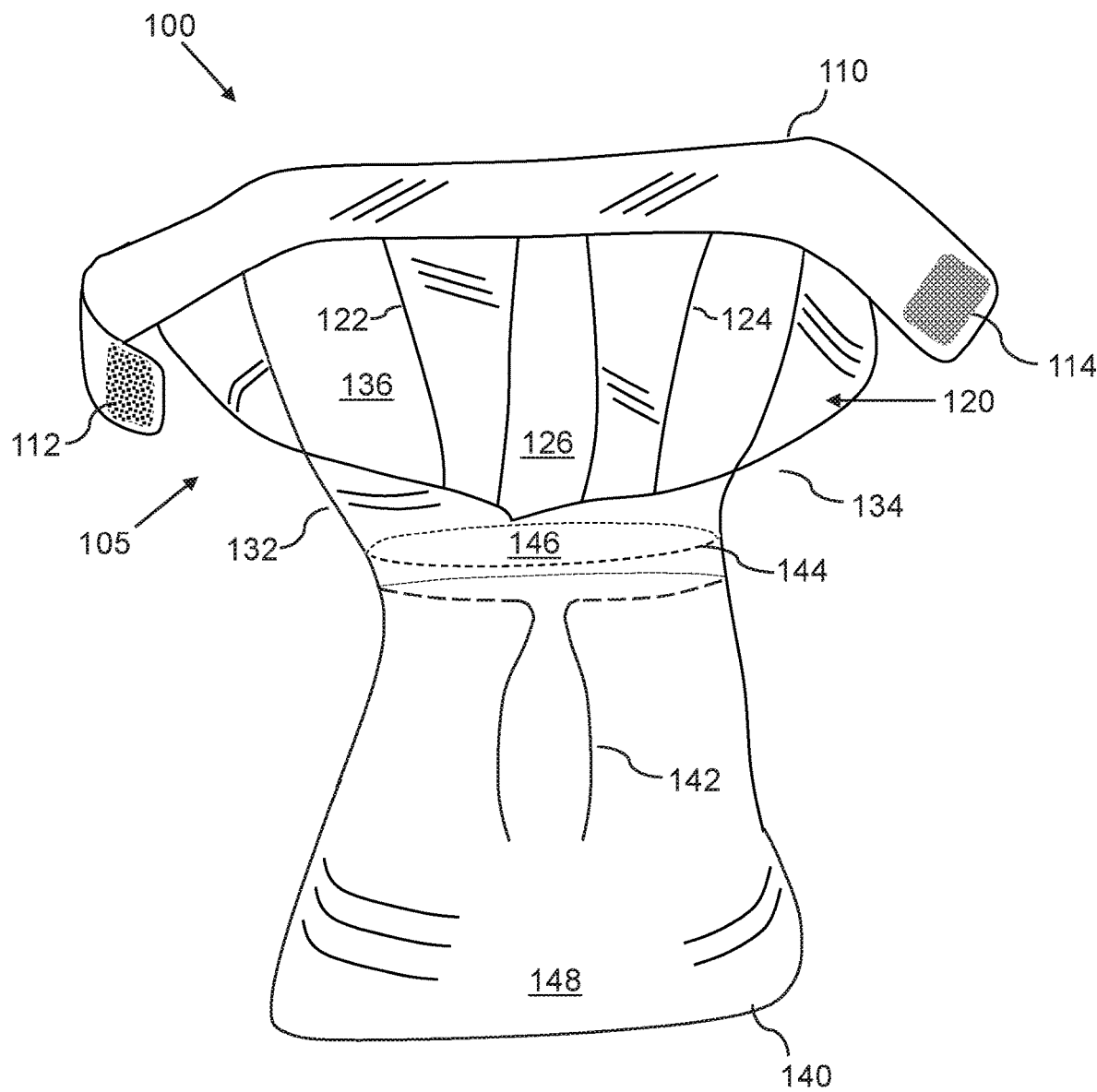
FIG. 1 is a bottom perspective view of a diaper for dogs and other pets with a waistband in an open configuration, according to an embodiment of the invention.

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide exemplary constructions. The embodiments are permissive rather than mandatory and illustrative rather than exhaustive.

In the following, we describe the structure of an embodiment of a diaper 100 for dogs and other pets with reference to FIG. 1, in such manner that like reference numerals refer to like components throughout; a convention that we shall employ for the remainder of this specification.

Figure 3:
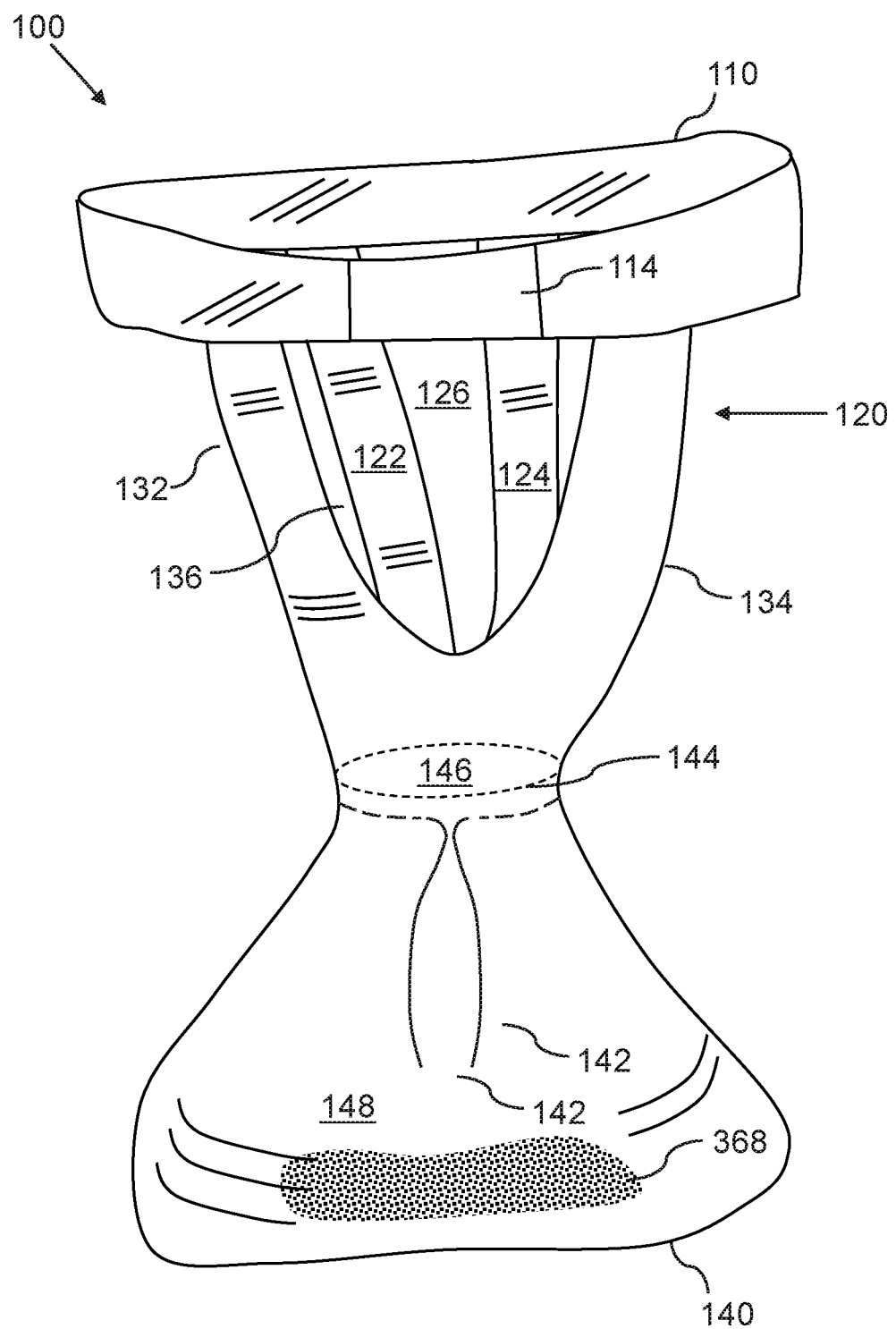
FIG. 3 is a bottom perspective view of a diaper for dogs and other pets with a waistband in a closed configuration, according to an embodiment of the invention.
Figure 4:
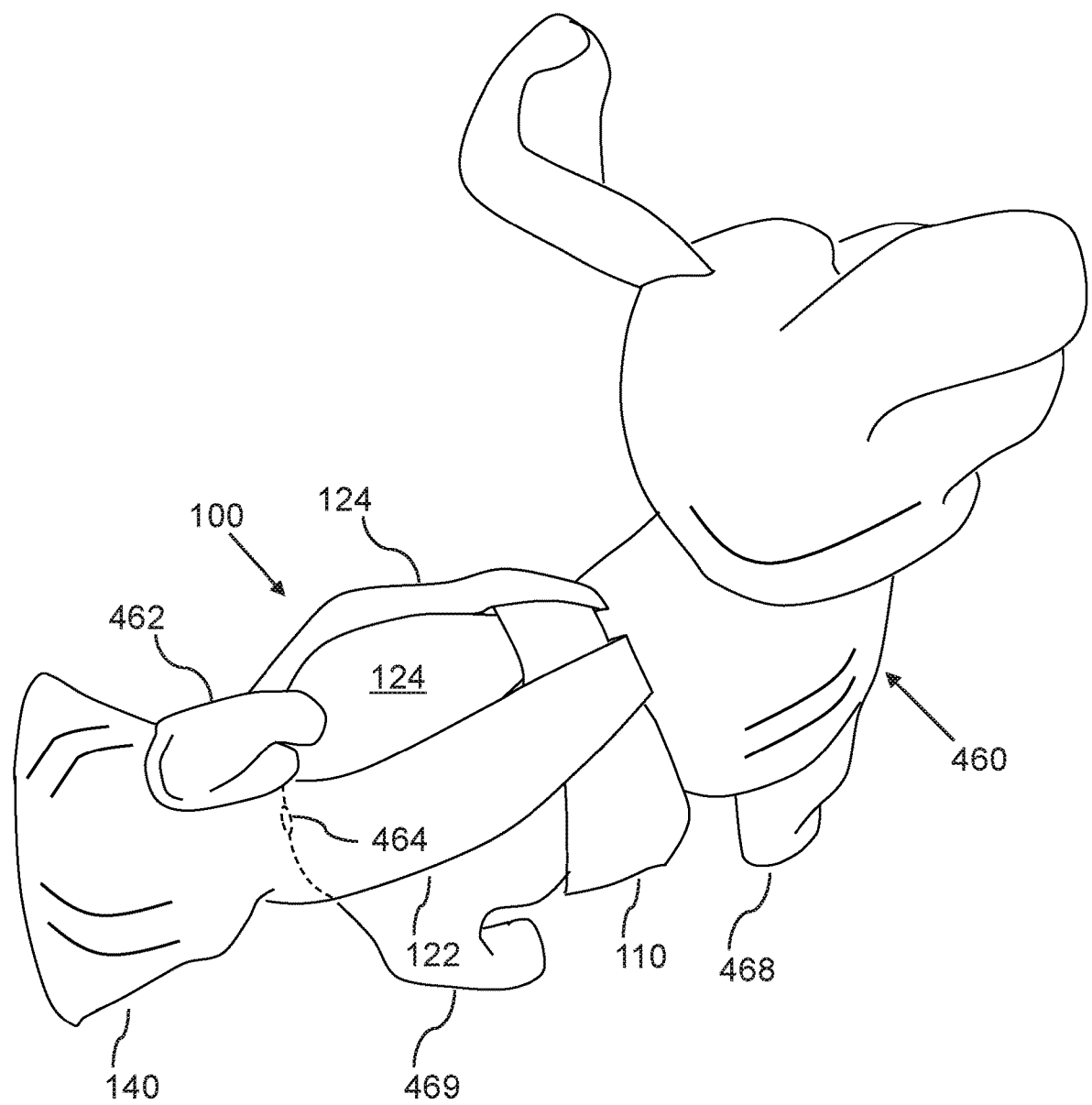
FIG. 4 is a top perspective view of a diaper for dogs mounted on a dog, according to an embodiment of the invention.

In an embodiment, as shown in FIG. 1, a dog diaper 100 can include:
  a) a waistband 110;
  b) a plurality of connector straps 120; and
  c) a collection bag 140 comprising an aperture 146 and an interior 148, such that the aperture 146 provides access to the interior 148, such that the connector straps 120 can be connected between the waistband 110 and the collection bag 140, such that upper ends of the connector straps are connected to the waistband and lower ends of the connector straps are connected to the collection bag 140;
  wherein the waistband 110, as shown in FIG. 4, can be configured to be positioned around the waist of a dog 460, in a front of rear legs 469 of the dog, and to a rear of front legs 468 of the dog 460;
  such that the aperture 146 of the collection bag 140 is configured to be positioned around an anus/rectal exit 464 of the dog 460, as shown in FIG. 4;
  whereby fecal matter 368 will be deposited in an interior 148 of the collection bag 140, as shown in FIG. 3, when the dog sits to defecate.

In a related embodiment, as show in FIG. 1, the waistband 110 can be open with connector portions 112 114 on first and second ends of the waistband 110, such that the connector portions 112 114 are configured to detachably connect the first and second ends.

Figure 2:
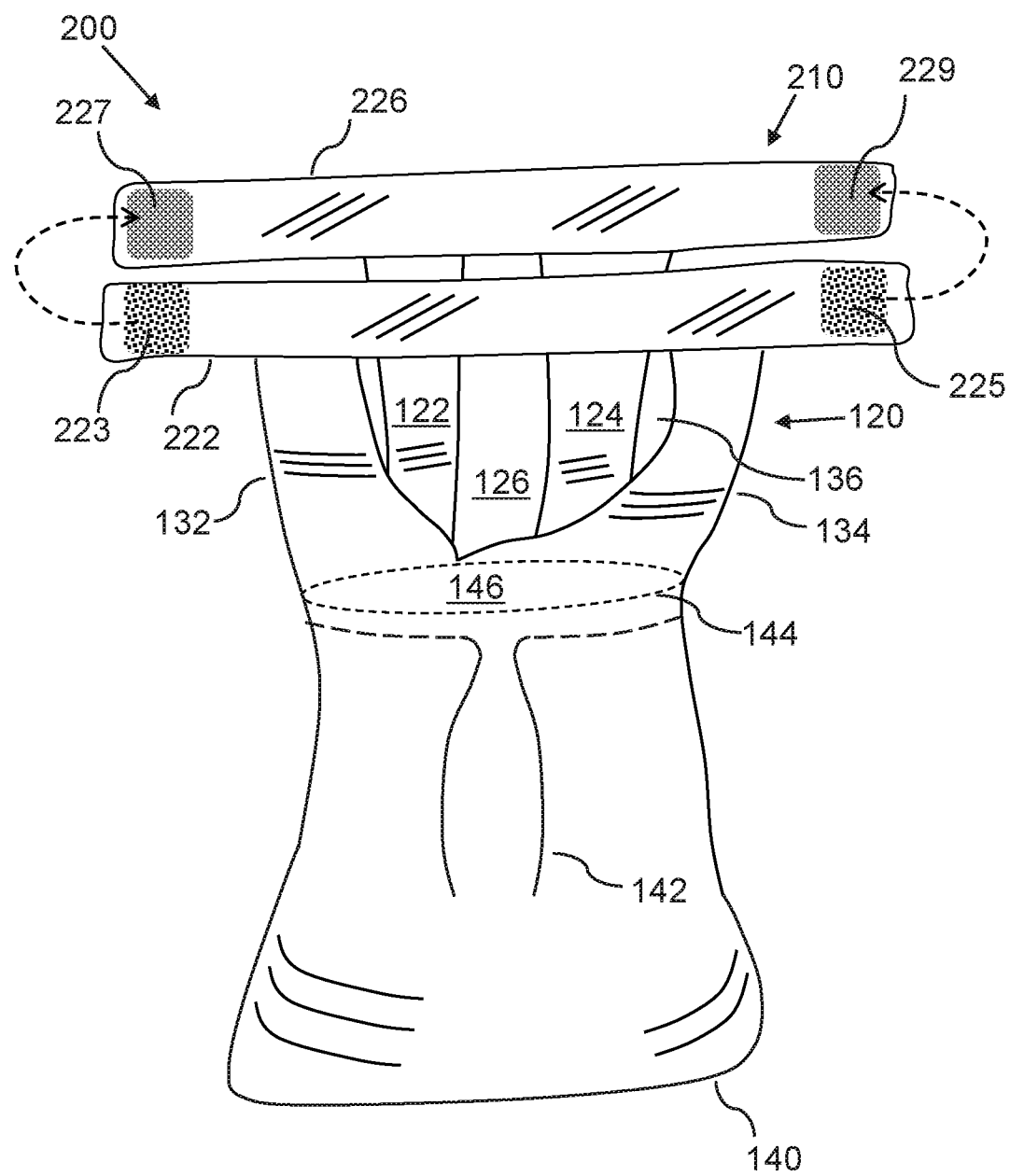
FIG. 2 is a bottom perspective view of a diaper for dogs and other pets with a waistband in an open configuration, according to an embodiment of the invention.

In a related embodiment, as show in FIG. 2, the waistband 210 can include:
  a) a bottom waistband portion 222, including bottom first and second connector portions 223 225 positioned on respectively bottom first and second ends of the bottom waistband portion 222; and
  b) a top waistband portion 226, including top first and second connector portions 227 229 positioned on respectively top first and second ends of the top waistband portion 226;
  such that the bottom first and top first connector portions 223 227 are configured to detachably connect the bottom first and top first ends; and
  such that the bottom second and top second connector portions 225 229 are configured to detachably connect the bottom second and top second ends.

In a further related embodiment, the connector portions 112 114 can be configured as hook and loop fasteners 112 114, such that a first connector portion 112 is a hook or loop portion 112, which connect to a second connector portion 114, which is respectively a loop or hook portion 114.

In another further related embodiment, at least one of the connector portions 112 114 can be configured as a patch of pressure sensitive adhesive 112 114.

Figure 5:
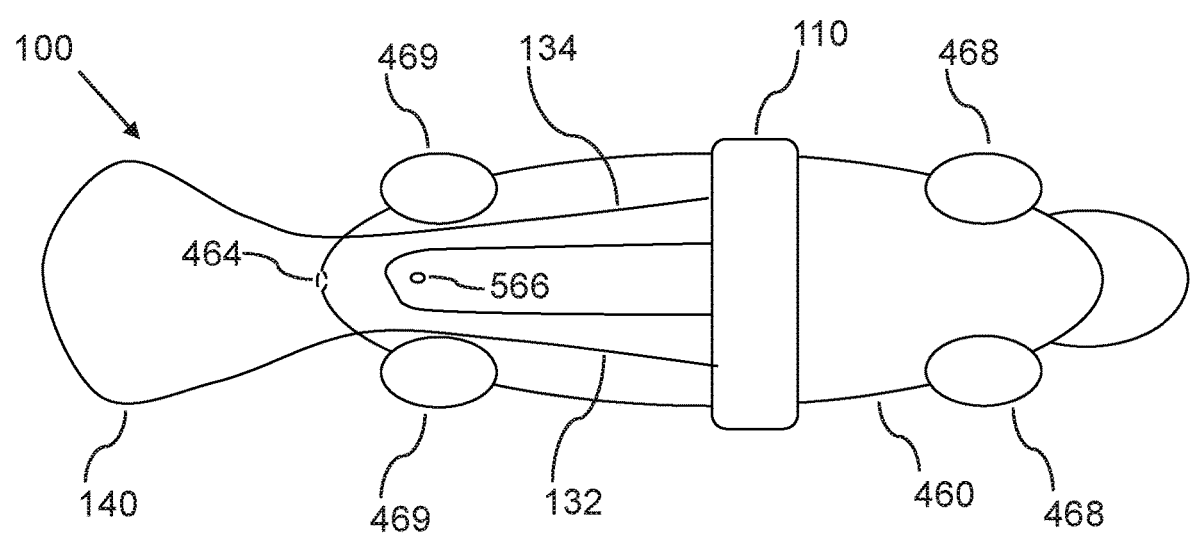
FIG. 5 is a bottom view of a diaper for dogs mounted on a dog, according to an embodiment of the invention.

In a related embodiment, the plurality of connector straps 120 can include:

a) first and second top straps 122 124, such that a top opening 126 between the first and second top straps 122 124 provides space for a tail 462 of the dog 460, as shown in FIG. 4; and
  b) first and second bottom straps 132 134, such that a bottom opening 136 between the first and second bottom straps 132 134 is configured to provide space for an external urethral opening 566 of the dog 460, as shown in FIG. 5, such that urine emitted from the external urethral opening 566 is not collected in the collection bag 140.

In a related embodiment, the waistband 110, connector straps 120, and/or collection bag 140 can be made of plastic, which can be a recyclable or biodegradable plastic. The waistband 110, connector straps 120, and collection bag 140 can for example be stamped out from a single elongated plastic bag.

Figure 8:
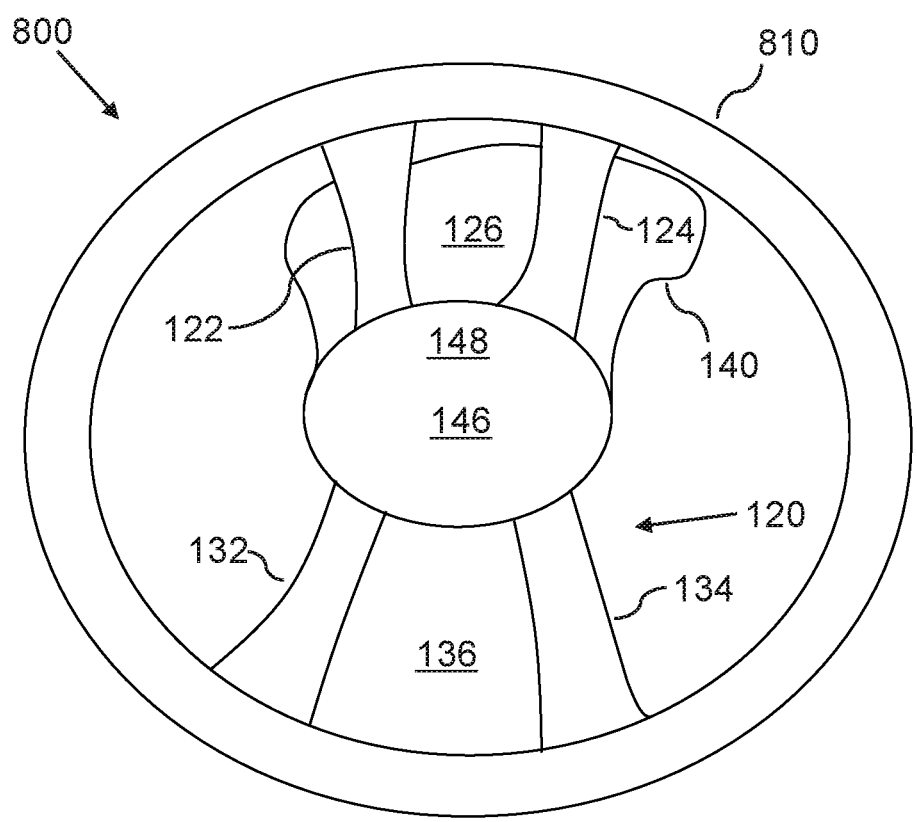
FIG. 8 is a front view of a diaper for dogs and other pets, according to an embodiment of the invention.

In a related embodiment, the waistband 110 can be an elastic strap. In related embodiments, as shown in FIG. 8, the waistband 810 can be configured as one closed piece, without any openings or connector portions.

In a related embodiment, the waistband 110 can be one and a half inch wide or configured with a width in a range of 1-4 inches.

In a related embodiment, an upper part of the collection bag 140 can further include a drawstring 142, which is mounted around a first circumference of the collection bag, such that pulling on the drawstring 142 closes the collection bag 140, whereby the collection bag 140 can be closed by pulling on the drawstring 142 after fecal matter has been deposited in the collection bag 140.

In a related embodiment, an upper part of the collection bag 140 can further include a perforation 144 around a second circumference of the collection bag, such that pulling on the collection bag 140 can release a lower part of the collection bag 140 by tearing the lower part of at the perforation 144. In a further related embodiment, the perforation 144 can be positioned above the drawstring 142, whereby the collection bag can be closed by pulling on the drawstring 142 after fecal matter has been deposited in the collection bag 140, and the closed collection bag 140 can then be removed by pulling it off at the perforation 144.

In a related embodiment, FIG. 4 shows a top perspective view of the dog diaper 100 mounted on a dog 460, showing how the first and second top straps 122 124 go across the back of the dog 460.

In a related embodiment, FIG. 5 shows a bottom view of the dog diaper 100 mounted on a dog 460, showing how the first and second bottom straps 132 134 go across the underside/belly of the dog 460.

Figure 6:
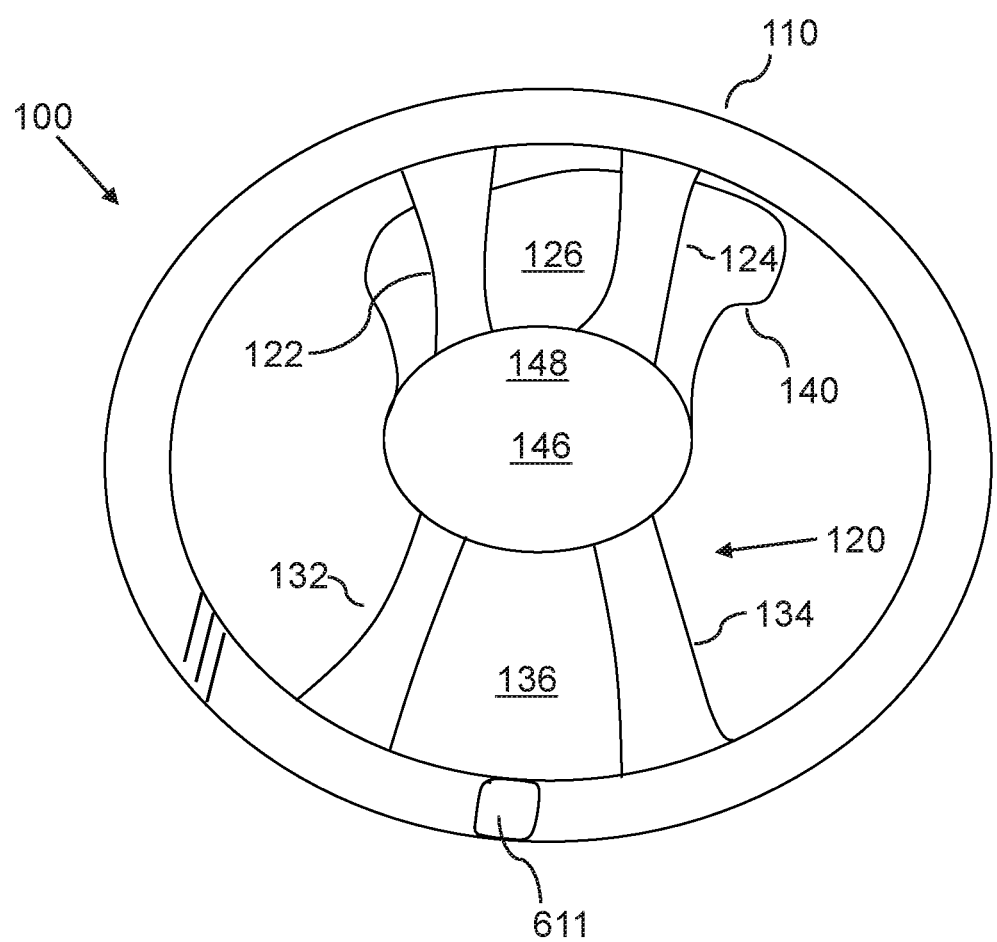
FIG. 6 is a front view of a diaper for dogs and other pets with a waistband in a closed configuration, according to an embodiment of the invention.

In a related embodiment, FIG. 6 shows a front view of the dog diaper 100, with a single band connector 611, formed by the connector portions 112 114. In further related embodiment, other positions of a single band connector 611 are possible, such as on a top or side, and should be considered fully included in the scope of this disclosure.

Figure 7:
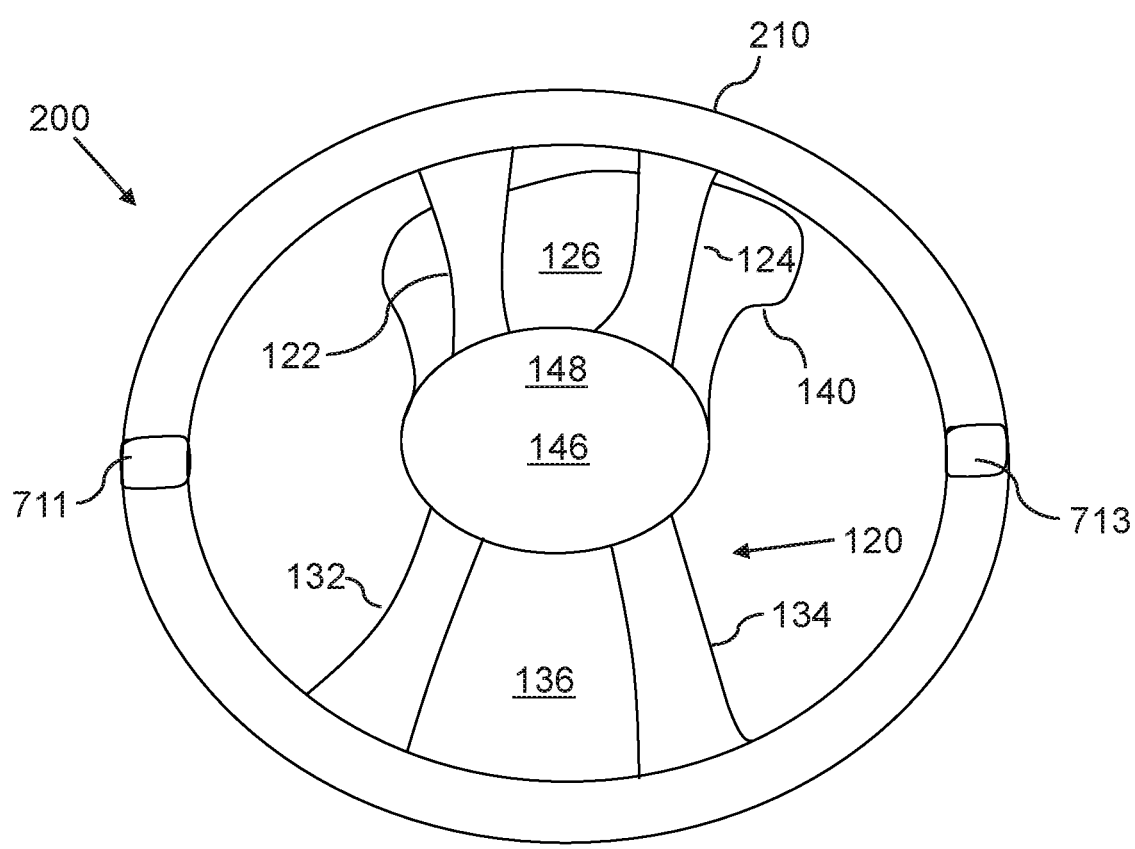
FIG. 7 is a front view of a diaper for dogs and other pets with a waistband in a closed configuration, according to an embodiment of the invention.

In another related embodiment, FIG. 7 shows a front view of the dog diaper 200, with a first band connector 711 formed by the bottom first and top first connector portions 223 227 and a second band connector 713 formed by the bottom second and top second connector portions 225 229. In further related embodiment, other positions of a dual band connectors 711 713 are possible, such as on a top or side, and should be considered fully included in the scope of this disclosure.

In a related embodiment, FIG. 8 shows a front view of the dog diaper 800 with a closed single piece waistband 810, without any band connectors.

Thus, in an embodiment, as shown in FIG. 1, a dog diaper 100 can include:
a) a mounting harness 105, which for example can include a waistband 110 and a plurality of connector straps 120, such that the mounting harness 105 is configured to be mounted on the dog; and
b) a collection bag 140 comprising an aperture 146 and an interior 148, such that the aperture 146 provides access to the interior 148;
such that the collection bag 140 is connected to the mounting harness 105;
such that the aperture 146 of the collection bag 140 is configured to be positioned around an anus/rectal exit 464 of the dog 460, as shown in FIG. 4;
whereby fecal matter 368 will be deposited in an interior 148 of the collection bag 140, as shown in FIG. 3, when the dog sits to defecate.

In various related embodiments, the dog diaper 100 200 800 gathers and collects the feces of dogs but does not collect urine. It is easy to put on the dog and easy to remove. The urethra is exposed, which allows the dog to urinate freely. As the dog sits down to defecate, the feces will fall into the collection bag 140. As the dog finishes their bowel movement, the dog owner can pull on the string, which will tighten the bag and gather the feces; which makes for an easy disposal.

Here has thus been described a multitude of embodiments of the dog diaper 100 and methods related thereto, which can be employed in numerous modes of usage.

The many features and advantages of the invention are apparent from the detailed specification, and thus, it is intended by the appended claims to cover all such features and advantages of the invention, which fall within the true spirit and scope of the invention.

Many such alternative configurations are readily apparent and should be considered fully included in this specification and the claims appended hereto. Accordingly, since numerous modifications and variations will readily occur to those skilled in the art, the invention is not limited to the exact construction and operation illustrated and described, and thus, all suitable modifications and equivalents may be resorted to, falling within the scope of the invention.

What is claimed is:

1. A diaper for mounting on a dog, the diaper comprising:
a) a waistband;
b) a plurality of connector straps, comprising:
first and second top straps, such that a top opening between the first and second top straps is configured to provide space for a tail of the dog; and
first and second bottom straps, such that a bottom opening between the first and second bottom straps is configured to provide space for an external urethral opening of the dog; and
c) a collection bag, comprising an aperture and an interior; such that the aperture provides access to the interior;
such that the connector straps are connected between the waistband and the collection bag, such that upper ends of the connector straps are connected to the waistband and lower ends of the connector straps are connected to the collection bag;
whereby the waistband is configured to be positioned around the waist of the dog, such that the aperture of the collection bag is positioned around a rectal exit of the dog, whereby fecal matter is deposited in the interior of the collection bag when the dog defecates;
wherein an upper part of the collection bag further comprises:
a drawstring, which is mounted around a first circumference of the collection bag;
such that pulling on the drawstring closes the collection bag, whereby the collection bag is closed by pulling on the drawstring after fecal matter has been deposited in the collection bag;
wherein the upper part of the collection bag further comprises a perforation around a second circumference of the collection bag;
wherein the perforation is positioned above the drawstring;
such that pulling on the collection bag releases a lower part of the collection bag by tearing the lower part of the collection bag off at the perforation.

2. The diaper of claim 1, wherein the waistband is open, such that the waistband further comprises connector portions on first and second ends of the waistband, such that the connector portions are configured to detachably connect the first and second ends.

3. The diaper of claim 2, wherein the connector portions are hook and loop fasteners.

4. The diaper of claim 1, wherein the waistband further comprises:
a) a bottom waistband portion, comprising bottom first and second connector portions positioned on respectively bottom first and second ends of the bottom waistband portion; and
b) a top waistband portion, comprising top first and second connector portions positioned on respectively top first and second ends of the top waistband portion;
such that the bottom first and top first connector portions are configured to detachably connect the bottom first and top first ends; and
such that the bottom second and top second connector portions are configured to detachably connect the bottom second and top second ends.

5. The diaper of claim 1, wherein the waistband is an elastic strap.

6. The diaper of claim 1, wherein the waistband is configured as one closed piece.

* * * * *